United States Patent [19]

Weaver

[11] 4,245,653
[45] Jan. 20, 1981

[54] METHOD AND APPARATUS FOR OBTAINING SPECIMENS OF ENDOMETRIAL TISSUE

[76] Inventor: Kenneth Weaver, 110 E. Holston Ave., Johnson City, Tenn. 37601

[21] Appl. No.: 355

[22] Filed: Jan. 2, 1979

[51] Int. Cl.³ .......................................... A61B 10/00
[52] U.S. Cl. ..................... 128/750; 128/756
[58] Field of Search ............... 128/749–752, 128/756–759

[56] References Cited

U.S. PATENT DOCUMENTS

| | | | |
|---|---|---|---|
| 2,739,585 | 3/1956 | Ayre | 128/756 |
| 2,955,591 | 10/1960 | MacLean | 128/756 |
| 3,074,396 | 1/1963 | MacLean | 128/304 X |
| 3,173,414 | 3/1965 | Guillant | 128/318X |
| 3,491,747 | 1/1970 | Robinson | 128/757 |
| 3,606,878 | 9/1971 | Kellogg, Jr. | 128/329 X |
| 3,636,940 | 1/1972 | Gravlee | 128/750 |
| 3,777,743 | 12/1973 | Binard et al. | 128/278 X |
| 3,796,211 | 3/1974 | Kohl | 128/749 |

FOREIGN PATENT DOCUMENTS 257747 3/1965 Australia .................. 128/751

*Primary Examiner*—Kyle L. Howell
*Attorney, Agent, or Firm*—Bell, Seltzer, Park & Gibson

[57] ABSTRACT

A method and apparatus for obtaining specimens of endometrial tissue and which comprises an elongate tubular member having a forward end adapted to be inserted into the cervical opening, and a curettage member slideably and rotatably disposed within the tubular member. The curettage member has a blade portion at the forward end and a crank at the rearward end, whereby the blade portion may be advanced into the uterine cavity and rotated about the axis of the cavity to sever tissue specimens along substantially the full length of the cavity. Also, the tubular member includes a connector for coupling a syringe, whereby a solution may be injected into the uterine cavity and subsequently aspirated back into the syringe along with the entrained severed tissue specimens.

13 Claims, 5 Drawing Figures

METHOD AND APPARATUS FOR OBTAINING SPECIMENS OF ENDOMETRIAL TISSUE

The present invention relates to a method and apparatus for obtaining specimens of endometrial tissue for pathological examination or the like, and which is particularly useful in diagnosing various types of intrauterine cancer, such as endometrial carcinoma.

For many years, it has been common to obtain specimens of endometrial tissue for examination as part of a dilitation and curettage (D & C) procedure, which is performed in the operating suite using a general anesthesia. However, the recent finding of a greatly increased incidence of cancer of the endometrium, has created the need for a more simple, less expensive procedure, and which is capable of routine outpatient use so as to provide the opportunity for detection of the disease in its initial stages.

Recently, several devices have been proposed in an attempt to satisfy this need. One such device comprises a fenestrated tube which is designed to be inserted into the uterine cavity, and a suction is then applied to the tube to draw sample tissue specimens through the openings and into the tube. In another procedure, the uterine cavity is irrigated with a saline solution so as to collect loose cells with the solution, and the cells are subsequently separated from the solution for examination. Neither of these procedures is totally satisfactory however, since only loose surface cells are collected, and such cells can only be examined in the manner of a routine cervical smear. In other words, the specimens are not severed or cut from the endometrium, and they do not include a full thickness section which is necessary to permit examination in the manner of a biopsy specimen.

A rotary brush device has also been proposed for collecting tissue specimens, which comprises a bladelike member which is rotated to scrape the uterine cavity. The tissue specimens adhere to the member and are subsequently transferred onto a slide for examination. However, this device is not totally satisfactory since it requires several placements to obtain samples from the entire uterine cavity. Also, the procedure can be painful to many patients.

It is accordingly an object of the present invention to provide a method and apparatus for sampling endometrial tissue, which may be performed on an outpatient basis, and which is simple, effective, and yet inexpensive.

It is a more particular object of the present invention to provide a method and apparatus for sampling endometrial tissue which obtains intact specimens of severed tissue, as opposed to merely loose surface cells, to thereby permit examination in the manner of a biopsy.

It is also an object of the present invention to provide a method and apparatus for sampling endometrial tissue which obtains specimens from substantially all areas of the uterine cavity with a single insertion, and which is not unduly uncomfortable to the patient.

These and other objects and advantages of the present invention are achieved in the embodiment illustrated herein by the provision of an apparatus which comprises a tubular member having a forward end which is adapted to be inserted into the cervical opening. A curettage member is slideably and rotatably mounted within the tubular member, and comprises a rod extending along the length of the tubular member, a blade portion at the forward end of the rod and which is normally disposed adjacent the forward end of the tubular member, and a handle disposed at the opposite rearward end of the rod so as to be positioned outwardly beyond the rearward end of the tubular member. By this arrangement, the curettage member may be moved between a retracted position wherein the blade portion is disposed within the tubular member and an advanced position wherein the blade portion is disposed forwardly of the tubular member forward end, and the blade portion may then be rotated by rotation of the handle. The apparatus further comprises means for selectively injecting a liquid into the uterine cavity, and subsequently aspirating the liquid from the cavity.

In use, the curettage member is initially retracted so that the blade portion is enclosed within the forward end of the tubular member, and the forward end is then inserted into the cervical opening. A solution, such as an isotonic saline solution with a suitable local anesthesia, is then injected into the cavity. The blade portion is then advanced and rotated to sever the specimens, and the solution and entrained specimens are then aspirated from the cavity, where the specimens are separated for pathological examination in the conventional manner. Preferably, the blade portion has a length generally corresponding to the length of the uterine cavity so as to permit sampling of substantially all of the surface of the uterine cavity with a single insertion.

Some of the objects having been stated, other objects will appear as the description proceeds, when taken in connection with the accompanying drawings in which FIG. 1 is a perspective view of an apparatus embodying the features of the present invention;

Figure 1:
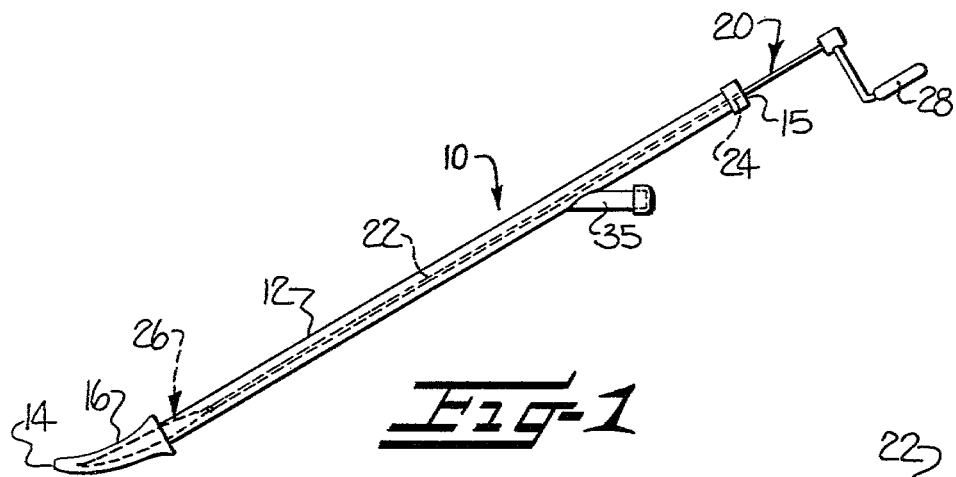

Referring more specifically to the drawings, an apparatus embodying the features of the present invention is illustrated generally at 10. Preferably, the entire apparatus is fabricated from inexpensive plastic or metallic materials which permit it to be discarded after a single use. However, if desired, the apparatus could be fabricated from a suitable metallic material which would permit it to be sterilized for re-use.

The apparatus 10 comprises an elongate tubular member 12 having a forward end 14, and a rearward end 15. The forward portion of the member 12 is composed of a separate segment 16 of molded plastic or the like, and which is adapted to be inserted into the cervical opening. The rearward portion of the segment 16 includes an annular shield 18 for limiting the length to which it may be inserted.

A curettage member 20 is slideably and rotatably mounted within the tubular member 12, and comprises a central rod 22 coaxially disposed within the tubular member 12. The rod 22 has a length generally corresponding to the length of the tubular member, and it extends rearwardly through a sealing member 24 which is fixed in the interior of the tubular member at the rearward end 15. The curettage member further comprises a blade portion 26 mounted at the forward end of the rod 22, and handle means in the form of a crank 28 fixed to the opposite end of the rod and rearwardly of the tubular member 12.

Figure 2:
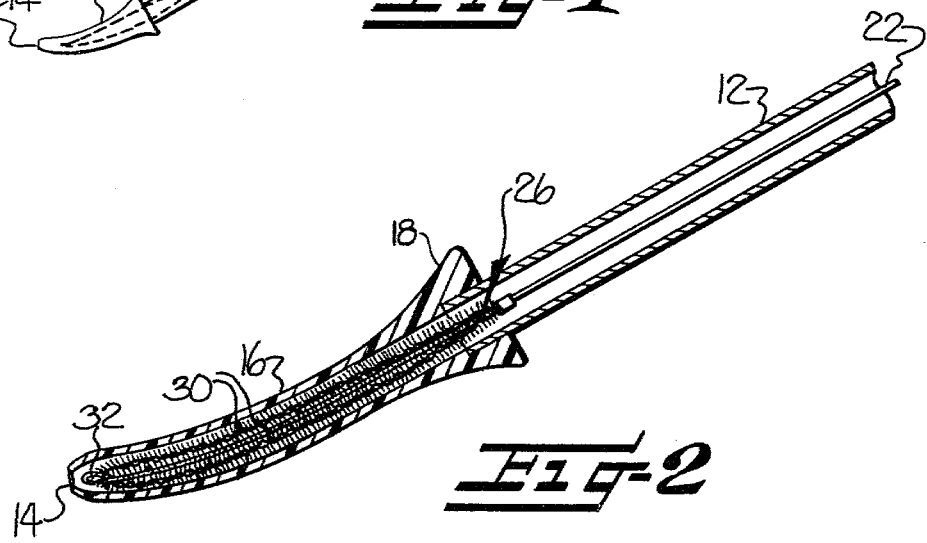
FIG. 2 is an enlarged sectional view of the forward end portion of the apparatus, and with the blade portion being retracted.

As illustrated in FIGS. 1 and 2, the curettage member 20 is disposed in a retracted position wherein the blade portion 26 is disposed within the segment 16 of the tubular member. By manually pushing forwardly on the crank 28 while holding the tubular member 12 stationary, the curettage member 20 may be moved forwardly to an advanced position wherein the crank 28 abuts the rearward end 15 of the tubular member and the blade portion 26 is disposed forwardly of the tubular member forward end 14, note FIG. 3. Thus the rearward end 15 serves as an abutment which limits the forward advance of the curettage member and thus the length to which the blade portion 26 extends beyond the forward end 14 in its advanced position. The curettage member may be moved rearwardly back to its retracted position by simply reversely pulling upon the crank 28.

Figure 3:
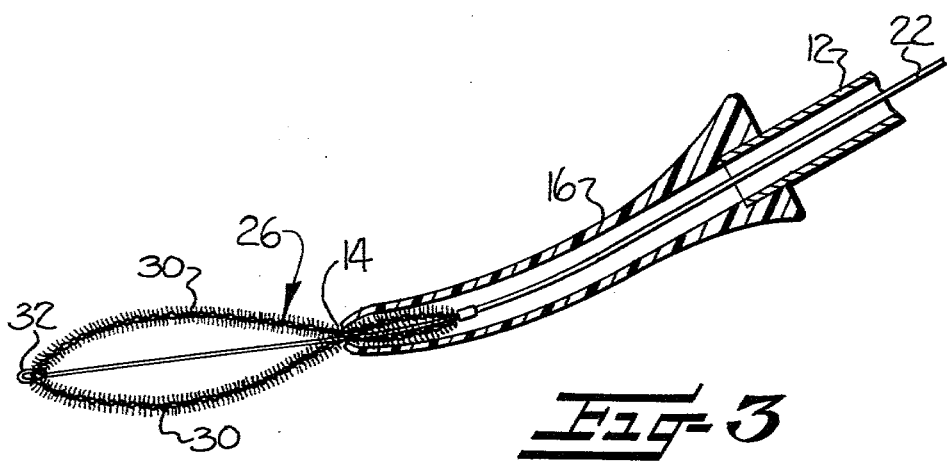
FIG. 3 is a view similar to FIG. 2, but with the blade portion advanced.
Figure 5:
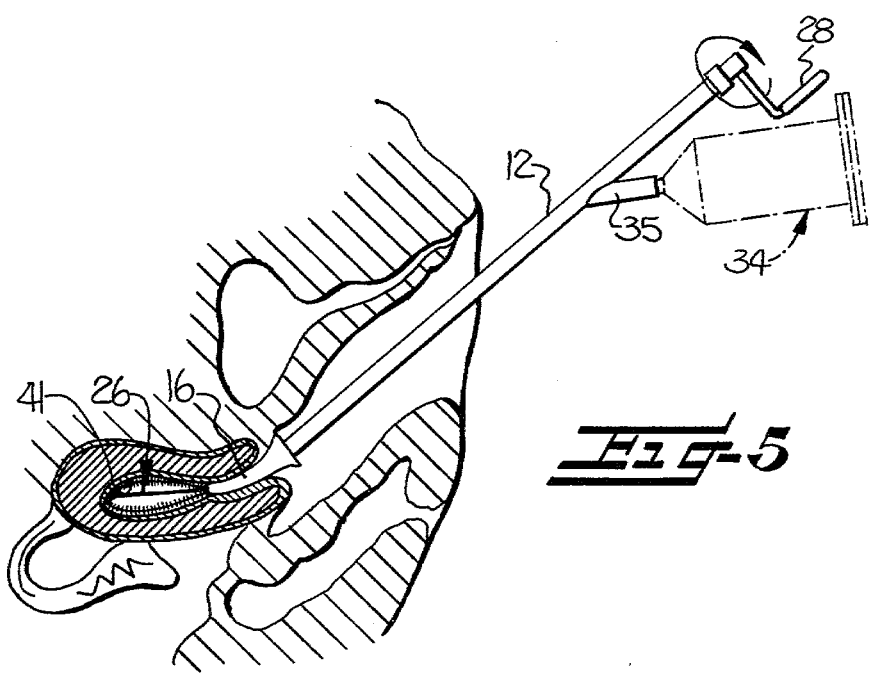
FIG. 5 is a view similar to FIG. 4, and illustrating the apparatus with the blade portion advanced to its operative position.

In the illustrated embodiment, the blade portion 26 comprises a pair of arcuately curved arms 30, which are self-biased for radial expansion into an elliptical configuration upon the blade portion being advanced from the forward end 14 of the tubular member, note FIGS. 3 and 5. More particularly, the two ends of the arms 30 are affixed to each other, with the forward ends being fixed to an enlarged, protective tip 32 at the forward end of the rod 22. The rear ends of the arms 30 are preferably fixed together but are free of any rigid connection with the rod 22 so as to permit relative sliding movement as the arms radially expand and contract. The arms themselves include means along substantially their entire length for severing specimens of the endometrium tissue upon rotation in the manner hereinafter described. As illustrated, the arms 30 are fabricated from spring steel wire having relatively rigid bristles affixed thereto for this purpose. Alternatively, they may comprise serrated plastic strips, or any other flexible material which is able to sever the tissue.

It is preferable that the exposed length of the arms 30 in the advanced position generally correspond to the length of the particular uterine cavity, in which it is to be used, note FIG. 5. Thus the apparatus of the present invention may be supplied to the physician in various sizes (i.e. various exposed blade lengths in the fully advanced position) so that the proper length may be selected for a particular patient. Alternatively, the rod 22 adjacent the crank 28 may include indicia (not shown) by which the exposed length of the blade may be visibly indicated to the physician and so that the exposed length of the blade may be manually controlled.

The apparatus 10 further comprises means mounted on the tubular member 12 for selectively coupling a syringe 34 or the like for liquid communication with the interior of the tubular member. As illustrated, this coupling means comprises a side tubular connector 35 which communicates with the interior of the tubular member. The connector 35 is adapted to matingly receive a standard syringe, and may be a Luer-lok connector as known in the art.

Figure 4:
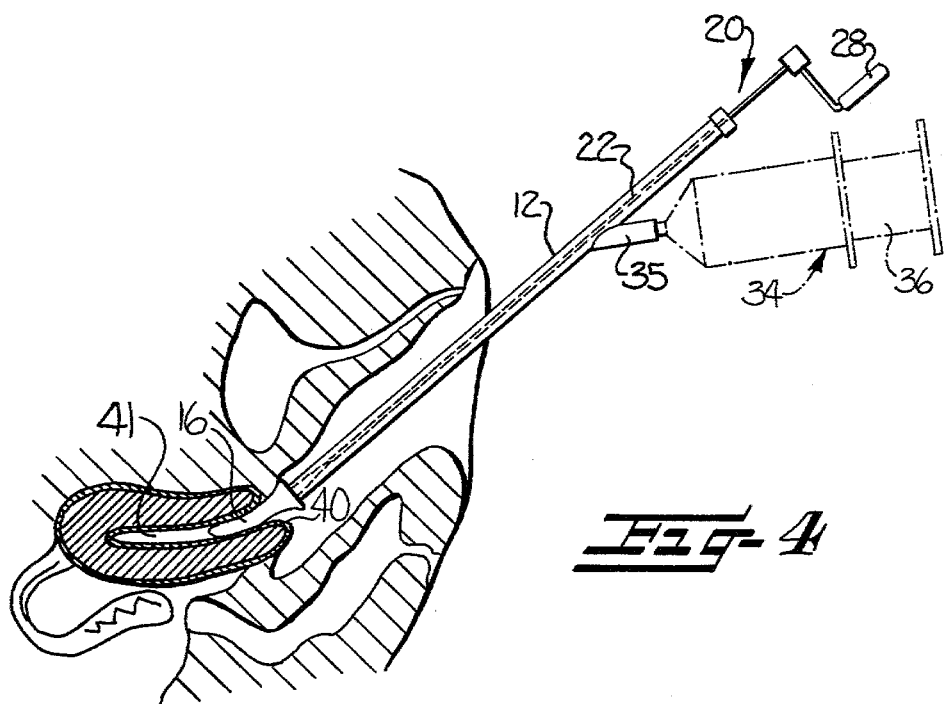
FIG. 4 is a perspective view, partly sectioned, illustrating the manner in which the apparatus of the present invention is inserted into the cervical opening.

To describe in more detail the steps of the operative procedure of the present invention, the segment 16 at the forward end of the apparatus is initially inserted into the cervical opening 40 in the manner illustrated in FIG. 4. In this regard, it will be noted that the curettage member is fully retracted so that the blade portion 26 is fully enclosed in the segment 16. A syringe 34 having a suitable quantity of a solution therein, is affixed to the connector 35 and the solution is then injected into the uterine cavity 41 from the forward end of the tubular member by depressing the plunger 36 of the syringe. The blade portion 26 is then advanced by manually advancing the crank 28 forwardly until it engages the rearward end 15 of the tubular member. As noted above, the amount of the advance is predetermined to control the length to which the blade portion 26 is inserted into the uterine cavity 41, and preferably the length is chosen so as to generally correspond to the length of the uterine cavity. The crank 28 is then rotated, resulting in the blade portion being correspondingly rotated about the axis of the uterine cavity. The rotating blade portion serves to sever tissue specimens from the surface of the cavity, which become entrained in the solution.

To retrieve the solution and severed tissue specimens, the plunger 36 is withdrawn, causing the solution and specimens to be aspirated into the tubular member through the forward end 14 and then into the syringe 34. The specimens are then separated from the solution by filtration or other conventional procedure, to permit them to be examined for example by a pathologist in the manner of a biopsy.

The solution preferably comprises an isotonic saline solution which serves to preserve the tissue specimens without undue swelling. Also, a suitable local anesthesia may be added to the solution, such as 1% Xylocaine, to minimize discomfort to the patient. In such case, the physician should delay for about two minutes after the solution is injected and before rotating the blade portion, in order to provide time for the anesthesia to become effective.

In the drawings and specification, there has been set forth a preferred embodiment of the invention, and although specific terms are employed, they are used in a generic and descriptive sense only and not for purposes of limitation.

That which is claimed is:

1. An apparatus for obtaining specimens of endometrial tissue for pathological examination or the like, and comprising a tubular member having an open forward end adapted to be inserted into the cervical opening, and a rearward end, curettage means slideably and rotatably mounted within said tubular member, said curettage means including a forward blade portion disposed adjacent said tubular member forward end and handle means disposed outwardly beyond said tubular member rearward end, said blade portion having means disposed along substantially its entire length for severing tissue specimens upon rotation thereof, whereby the curettage means may be selectively moved between a retracted position wherein said blade portion is disposed within said tubular member and an advanced position wherein said blade portion is disposed forwardly of said tubular member forward end, and whereby the blade portion may be rotated by rotation of said handle means to sever tissue on the surface of the uterine cavity, and means including a liquid container operatively associated with said tubular member for permitting a liquid in the container to be selectively injected into the uterine cavity and thereafter aspirated from the cavity and collected in the container, and while the forward end of said tubular member is inserted in the cervical opening, whereby the severed tissue specimens entrained with the collected liquid may be readily obtained for examination purposes.

2. The apparatus as defined in claim 1 further comprising abutment means between said tubular member and curettage means for limiting the forward advance of the curettage means with respect to the tubular member and thus the length to which the blade portion extends beyond said tubular member forward end in said advanced position.

3. The apparatus as defined in claim 2 wherein the length to which the blade portion extends beyond said tubular member forward end in said advanced position is predetermined so as to generally correspond to the length of a particular uterine cavity, whereby representative tissue specimens from substantially all of the surface of the uterine cavity may be obtained with a single insertion.

4. The apparatus as defined in claim 1 wherein said blade portion is self-biased for radial expansion and is constrained by said tubular member, and so that the blade portion radially expands upon being moved to said advanced position, and radially contracts upon being moved to said retracted position.

5. The apparatus as defined in claim 4 wherein said blade portion comprises a pair of oppositely biased arcuately curved arms which are attached to each other at their ends, and wherein the arms assume an elliptical configuration in said advanced position and are substantially contiguous along their length in said retracted position.

6. The apparatus as defined in claim 5 wherein each of said arms includes said severing means positioned along substantially its entire length for severing specimens of the endometrial tissue upon said handle means being rotated.

7. An apparatus for obtaining specimens of endometrial tissue for pathological examination or the like, and comprising
a tubular member having an open forward end adapted to be inserted into the cervical opening, and a rearward end,
curettage means slideably and rotatably mounted within said tubular member, said curettage means including a forward blade portion disposed adjacent said tubular member forward end and handle means disposed outwardly beyond said tubular member rearward end, said blade portion having means disposed along substantially its entire length for severing tissue specimens upon rotation thereof, whereby the curettage means may be selectively moved between a retracted position wherein said blade portion is disposed within said tubular member and an advanced position wherein said blade portion is disposed forwardly of said tubular member forward end, and whereby the blade portion may be rotated by rotation of said handle means to sever tissue on the surface of the uterine cavity,
a liquid syringe mounted for liquid communication with the interior of said tubular member, and
sealing means between the interior of said tubular member and said curettage means for precluding the passage of a liquid from said syringe outwardly through the rearward end of said tubular member, whereby a liquid may be injected from the syringe outwardly through the open forward end of said tubular member, and aspirated back through said forward end and to the syringe, and whereby said blade portion may be advanced into the uterine cavity and rotated about the axis of the cavity by manipulation of said handle means.

8. The apparatus as defined in claim 7 wherein said tubular member further comprises an external shield mounted adjacent but spaced from said forward end thereof, for limiting the distance which said forward end may be inserted into the cervical opening.

9. A method of severing and recovering specimens of endometrial tissue for pathological examination or the like, and comprising the steps of
positioning one end of a tubular member in communication with the cervical opening,
injecting a solution into the uterine cavity,
moving an elongate blade member from within the tubular member into the cervical opening, said blade member having tissue severing means disposed along substantially its entire length,
rotating the blade member within the cervical cavity about the axis of the cavity and so as to sever tissue specimens along substantially the full length thereof, and then
aspirating and collecting the solution and entrained severed tissue specimens from the cavity.

10. The method as defined in claim 9 wherein the step of rotating a blade member is conducted while the solution is in the uterine cavity.

11. The method as defined in claim 10 wherein the solution comprises an isotonic saline solution.

12. The method as defined in claim 11 wherein the solution includes a local anesthesia.

13. The method as defined in either claim 9 or 10 wherein the solution is injected into the uterine cavity through the tubular member, and the solution is aspirated from the cavity through the tubular member.

* * * * *